(12) United States Patent
Smith-Petersen

(10) Patent No.: US 12,629,510 B2
(45) Date of Patent: May 19, 2026

(54) APPARATUS FOR APPLYING ELECTRODE ARRAY TO USER, AND SYSTEMS AND METHODS COMPRISING SAME

(71) Applicant: NOVOCURE GMBH, Root (CH)

(72) Inventor: Kathryn Smith-Petersen, Portsmouth, NH (US)

(73) Assignee: NOVOCURE GMBH, Baar (CH)

( * ) Notice: Subject to any disclaimer, the term of this patent is extended or adjusted under 35 U.S.C. 154(b) by 363 days.

(21) Appl. No.: 18/392,874

(22) Filed: Dec. 21, 2023

(65) Prior Publication Data

US 2024/0216674 A1     Jul. 4, 2024

Related U.S. Application Data

(60) Provisional application No. 63/436,126, filed on Dec. 30, 2022.

(51) Int. Cl.
*A61N 1/04* (2006.01)
*A61N 1/36* (2006.01)

(52) U.S. Cl.
CPC ....... *A61N 1/0492* (2013.01); *A61N 1/36002* (2017.08)

(58) Field of Classification Search
CPC ..... A61N 1/0492; A61N 1/36002; A61N 1/06
See application file for complete search history.

(56) References Cited

U.S. PATENT DOCUMENTS

| | | | |
|---|---|---|---|
| 4,067,322 A | 1/1978 | Johnson | |
| 4,362,165 A | 12/1982 | Carmon et al. | |
| 2004/0122500 A1 | 6/2004 | Rouns | |
| 2012/0144551 A1 | 6/2012 | Guldalian | |
| 2014/0213875 A1* | 7/2014 | Freeman | A61B 5/6839 |
| | | | 600/386 |
| 2024/0416112 A1* | 12/2024 | Scholl | A47C 7/72 |

FOREIGN PATENT DOCUMENTS

EP     0194823 A2     9/1986

OTHER PUBLICATIONS

International Search Report and Written Opinion for PCT/US2023/085452, dated May 10, 2024.

* cited by examiner

*Primary Examiner* — Eugene T Wu
(74) *Attorney, Agent, or Firm* — Ballard Spahr LLP

(57) ABSTRACT

An apparatus for applying an electrode array to a body of a user comprises a compressible pad having a first side that is configured to face toward the user, and a second side that is configured to face away from the user. The compressible pad comprises a first portion and a second portion. The first portion has a first front facing side having a first front facing surface and a first back facing side having a first back facing surface. The first front facing side is spaced from the first back facing side in a front facing direction. The second portion has a second front facing side having a second front facing surface and a second back facing side having a second back facing surface. The first front facing side is configured to face toward the user. The first front facing side extends outwardly in the front facing direction to form an apex.

20 Claims, 5 Drawing Sheets

APPARATUS FOR APPLYING ELECTRODE ARRAY TO USER, AND SYSTEMS AND METHODS COMPRISING SAME

CROSS-REFERENCE TO RELATED APPLICATIONS

This application claims priority to and the benefit of the filing date of U.S. Provisional Application No. 63/436,126, filed Dec. 30, 2022, the entirety of which is hereby incorporated by reference herein.

FIELD

This application relates to apparatuses, systems, and methods for applying an electrode array to a user.

BACKGROUND

Tumor Treating Fields (TTFields) therapy is a proven approach for treating tumors using alternating electric fields at frequencies between 50 kHz-1 MHz, more commonly, 100-500 kHz. In current commercial systems, the alternating electric fields are induced by electrode assemblies (e.g., arrays of capacitively coupled electrodes, also called transducer arrays or electrode arrays) placed on opposite sides of a target region of the subject's body. When an AC voltage is applied between opposing electrode arrays, an AC current is coupled through the electrode arrays and into the subject's body.

Direct contact of the electrode array against the skin of the user, without any air pockets (e.g., bubbles) between the skin of the user and the electrode array, can be important for performance of treatment. Achieving this contact can be challenging, particularly when the subject is placing the electrode array on himself/herself. This challenge can be further complicated when applying the electrode array on hard-to-reach places, such as on the back. Thus, this difficulty can diminish the independence of the subject, requiring the subject to have another person (helper) position the electrode arrays. Accordingly, a way to assist a subject with properly applying one or more electrode arrays is desirable.

SUMMARY

TTFields are approved for the treatment of glioblastoma multiforme (GBM), and may be delivered, for example, via the OPTUNE® system (Novocure Limited, St. Helier, Jersey), which includes transducer arrays placed on the patient's shaved head. More recently, TTFields therapy has been approved as a combination therapy with chemotherapy for malignant pleural mesothelioma (MPM), and may find use in treating tumors in other parts of the body. For applications targeting tumors in the torso, larger electrode arrays than currently used with the OPTUNE® system may be beneficial.

Disclosed herein, in one aspect, is an apparatus for applying an electrode array to a body of a user. The apparatus comprises a compressible pad having a first side that is configured to face toward the user, and a second side that is configured to face away from the user. The compressible pad comprises a first portion and a second portion. The first portion has a first front facing side having a first front facing surface and a first back facing side having a first back facing surface. The first front facing side is spaced from the first back facing side in a front facing direction, wherein the second portion has a second front facing side having a second front facing surface and a second back facing side having a second back facing surface. The first front facing side is configured to face toward the user. The second portion defines a central void space extending from the second front facing surface toward the second back facing surface. The first front facing side extends outwardly in the front facing direction to form an apex. Either the first back facing surface of the first portion abuts the second front facing surface of the second portion, or at least a portion of the first back facing side of the first portion is received within the central void space of the second portion.

Also disclosed herein is a system comprising the apparatus and an electrode array coupled to the apparatus.

Also disclosed herein is a kit comprising the apparatus and at least one electrode array.

Also disclosed herein is a method of using the apparatus to apply an electrode array to a user, the electrode array comprising a skin-facing adhesive layer and an outer surface opposite the skin-facing adhesive layer, the skin-facing adhesive layer being configured for contacting skin of the user and having a peripheral edge. The method comprises coupling the outer surface of the electrode array to the first side of the compressible pad of the apparatus. The user can move toward the apparatus to initiate contact of the apparatus with skin of the user so that the skin of the user initially contacts an area of the skin-facing adhesive layer within, and spaced from, the peripheral edge of the skin-facing adhesive layer. The user can continue to move toward the apparatus until the peripheral edge of the skin-facing adhesive layer is in contact with the skin of the user. moving the user toward the apparatus to initiate contact of the apparatus with skin of the user wherein the skin of the user initially contacts an area of the skin-facing adhesive layer within, and spaced from, the peripheral edge of the skin-facing adhesive layer

Figure 1:
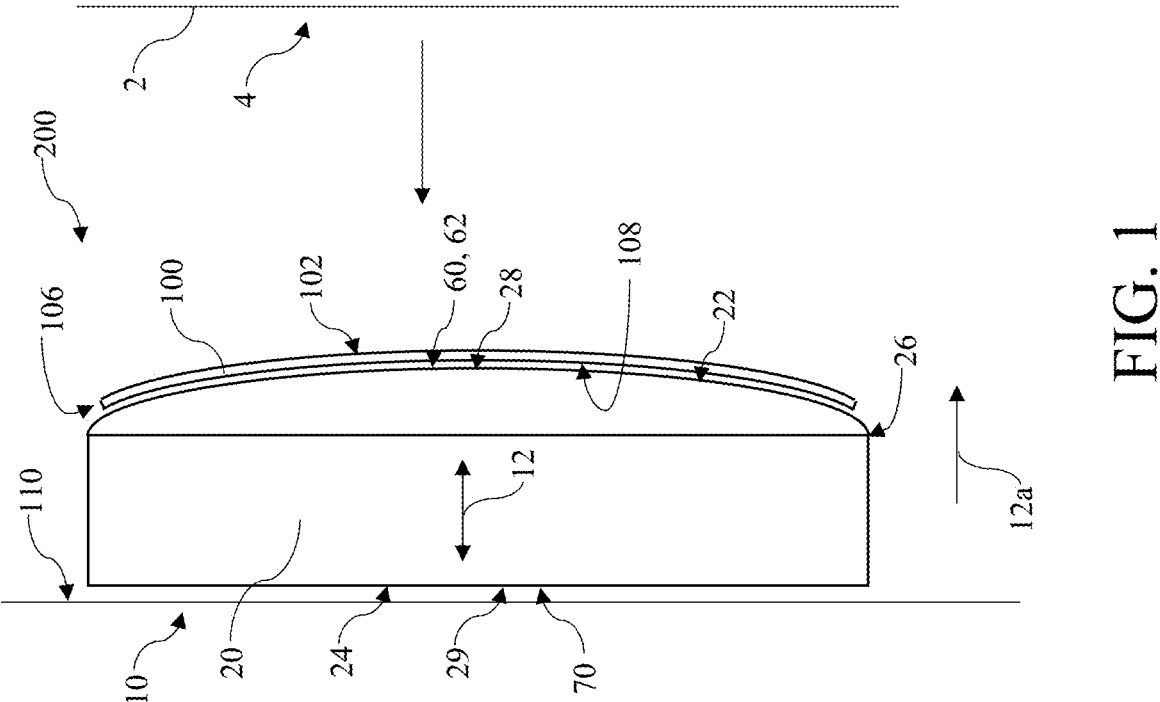
FIG. 1 is a schematic diagram of a system comprising an apparatus for applying an electrode array to skin of a user, as disclosed herein.

Various embodiments are described in detail below with reference to the accompanying drawings, wherein like reference numerals represent like elements, and wherein descriptions of like elements may not be repeated for every embodiment, but may be considered to be the same if previously described herein.

DESCRIPTION OF THE PREFERRED EMBODIMENTS

This application relates to positioning of electrode arrays that may be used, e.g., for delivering TTFields to a subject's body and treating one or more cancers or tumors located in the subject's body.

The present invention can be understood more readily by reference to the following detailed description, examples, drawings, and claims, and their previous and following description. However, it is to be understood that this invention is not limited to the specific apparatuses, devices, systems, and/or methods disclosed unless otherwise specified, and as such, of course, can vary.

Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

As used in the specification and the appended claims, the singular forms "a," "an," and "the" include plural referents unless the context clearly dictates otherwise.

Apparatus for Applying Electrode Array

Disclosed herein, with reference to FIG. 1, is an apparatus 10 for applying an electrode array 100 to a body 2 of a user. The electrode array 100 can have a skin-facing adhesive layer 102 and an outer surface 108 opposite the skin-facing adhesive layer 102, the skin-facing adhesive layer 102 being configured to contact and adhere to skin 4 of the user and having a peripheral edge 106. In some aspects, the skin-facing adhesive layer 102 may be present as one continuous layer that covers all of the electrode elements of the electrode array 100. The apparatus 10 can permit the user to apply the electrode array 100 with few or no air pockets between the skin-facing adhesive layer 102 of the electrode array 100 and the skin of the user. Accordingly, the apparatus 10 can be configured to position the electrode array 100 so that, as the user moves closer to, and contacts, the apparatus 10 and electrode array 100, a first portion of the skin-facing adhesive layer 102 of the electrode array 100 is first applied to the skin of the user. As the user continues to move in the same direction (as shown in FIG. 1) relative to the apparatus 10 and electrode array 100, the apparatus 10 can apply additional portions of the electrode skin-facing adhesive layer 102 of the electrode array 100 until an entirety of the skin-facing adhesive layer 102 of the electrode array 100 is in contact with the skin of the user. In some aspects, the first portion of the skin-facing adhesive layer 102 of the electrode array 100 that is first applied to the skin of the user can be a portion that is inwardly spaced from a peripheral edge 106 of the electrode array. Accordingly, in some aspects, the first portion of the skin-facing adhesive layer 102 of the electrode array 100 that is first applied to the skin of the user can be substantially centrally located on the skin-facing surface of the electrode array.

The apparatus 10 can comprise a compressible pad 20 having a first (front-facing) side 22 and a second side 24 spaced along a first axis 12. The first side 22 can be configured to face the user, and the second side 24 can be rear-facing. The front-facing side 22 can protrude (or otherwise extend) outwardly in a front facing direction 12a along the first axis 12 to form an apex 28. That is, the apex 28 can correspond to the portion of the first side 22 located at an outermost axial position moving in a front-facing direction 112a along the first axis 12. In some aspects, the first side 22 can have an outer perimeter 26. Optionally, in these aspects, the apex 28 can be spaced from the outer perimeter 26. That is, in such aspects, the apex 28 can be substantially centrally located on the first (front-facing) side 22. In some aspects, the apex 28 can be defined as a region of the first side 22 having a maximal offset along the first axis 12 from any portion of the second side 24 of the apparatus 10.

In some optional aspects, the compressible pad 20 illustrated in FIG. 1 can be formed from a single compressible material (e.g., foam). In other aspects, and referring to FIGS. 2-3, in some aspects, the compressible pad 20 can comprise a first portion 30 and a second portion 40. The first portion 30 can have a first front facing side 32 having a first front facing surface 34 and a first back facing side 36 having a first back facing surface 38. The second portion 40 can have a second front facing side 42 having a second front facing surface 44 and a second back facing side 46 having a second back facing surface 48. The first front facing side 32 (of the first portion) can protrude (or otherwise extend) outwardly in the front facing direction 12a to form an apex 28. That is, a portion of the first front facing side 32 can be spaced farthest from all parts of the second front facing side 42 in the front-facing direction 12a along or parallel to the axis 12 to form the apex 28. It is contemplated that the single compressible material can form the first portion 30, and the second portion 40 can cooperate with the first portion 30 to form the compressible pad 20 illustrated in FIG. 1. In some exemplary aspects, it is contemplated that the first front facing side 32 (of the first portion 30) as shown in FIGS. 2 and 4 can be provided as an embodiment of the first side 22 (of the compressible pad) as shown in FIG. 1.

In some aspects, the second portion 40 of the compressible pad 20 can define a central void space 50. In some optional aspects, the central void space 50 can extend continuously through the second portion 40 of the compressible pad 20 from the second front facing side 42 to the second rear facing side 46. In these aspects, the central void space 50 can extend continually from the second front facing surface 44 to the second back facing surface 48. In other aspects, the central void space 50 can extend only partially through the second portion 40 of the compressible pad 20 from the second front facing side 42 toward the second rear facing side 46.

Figure 2:
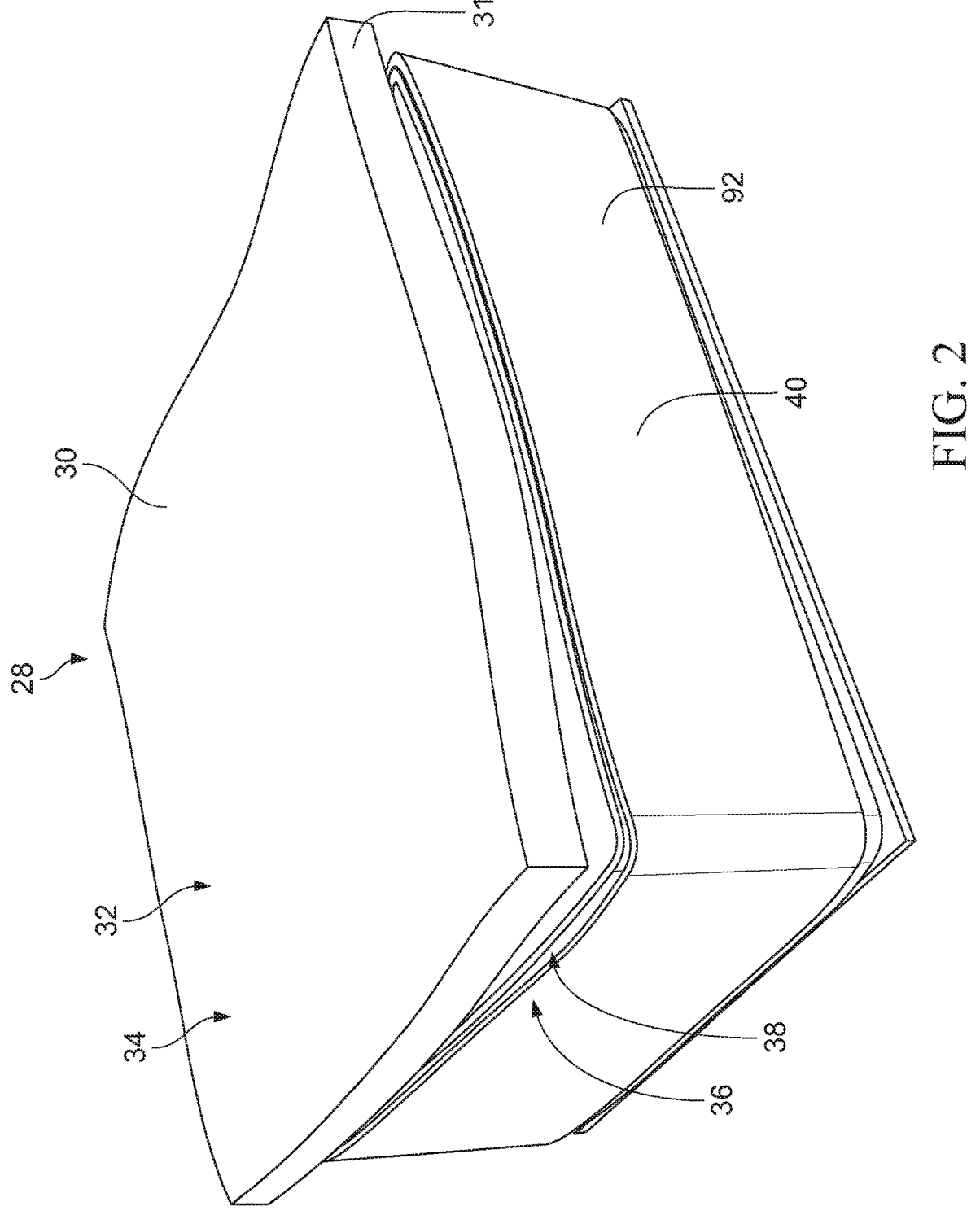
FIG. 2 is a perspective view of an exemplary apparatus for applying an electrode array to skin of a user, as disclosed herein.
Figure 3:
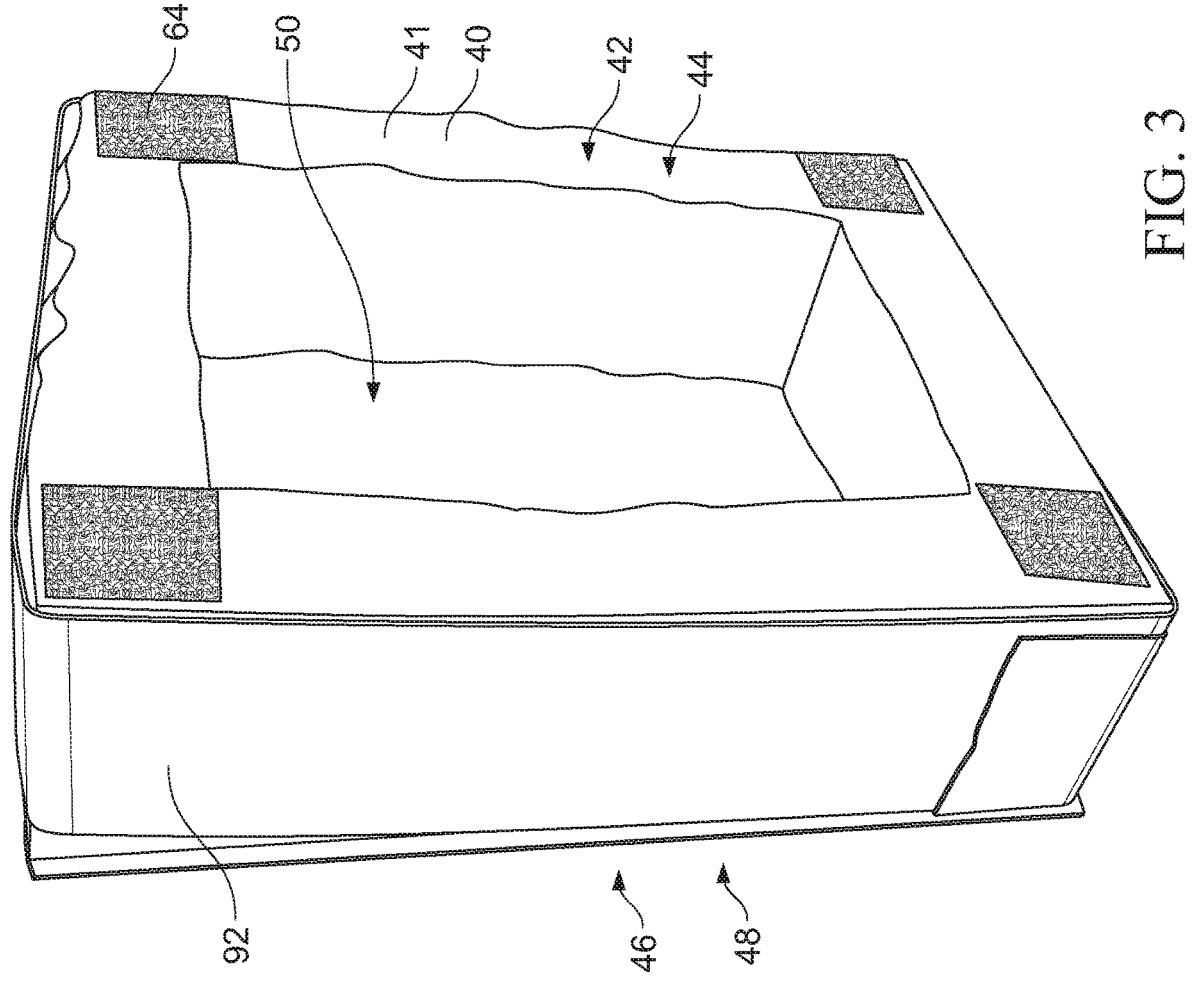
FIG. 3 is a perspective view of a portion of the apparatus of FIG. 2.
Figure 4:
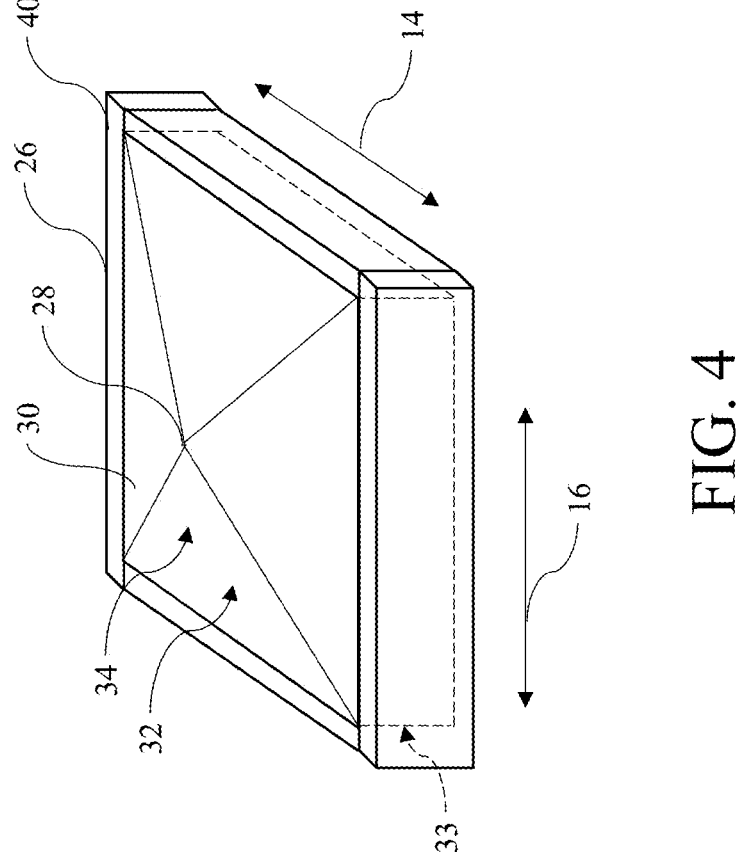
FIG. 4 is a perspective view of an exemplary apparatus for applying an electrode array to skin of a user, as disclosed herein.

As shown in FIGS. 2-3, in some aspects, the first back facing surface 38 of the first portion 30 of the compressible pad 20 can abut the second front facing surface 44 of the second portion 40. Referring to FIG. 4, in other aspects, at least a portion of the first back facing side 36 of the first portion can be received within the central void space of the second portion 40. Accordingly, in some aspects, the second portion 40 of the compressible pad 20 can peripherally surround at least a portion of the first portion 30 of the compressible pad.

Referring to FIGS. 1-2, it is contemplated that the first portion 30 of the compressible pad 20 can advantageously apply—or permit application of—the electrode array 100 so that few or no air pockets are formed between the skin-facing adhesive layer 102 of the electrode array 100 and the skin of the user, and the second portion 40 can apply a force to a peripheral edge 106 of the electrode array 100 to ensure adherence of the peripheral edge to the skin. This can inhibit the electrode array 100 from peeling from the skin at its outer edges.

In some aspects, the first portion 30 of the compressible pad 20 can have a first indentation load deflection, and the second portion 40 of the compressible pad 20 can have a second indentation load deflection that is greater than the first indentation load deflection of the first portion. The indentation load deflection can be defined as a force (in the direction of a thickness of the material) required to compress a material sample (e.g., a 4-inch thick material sample) by 25% of its thickness. Accordingly, in some aspects, the second portion 40 of the compressible pad 20 can be more firm than the first portion 30. In this way, the second portion 40 can apply a relatively large force against the peripheral edge 106 of the electrode array 100 (as compared to the forces applied to other portions of the electrode array 100 by the apparatus 10). In some aspects, the second indentation load deflection can be at least 10% greater than the first indentation load deflection. In some aspects, the second indentation load deflection can be at least 25% greater than, at least 50% greater than, at least 75% greater than, at least 100% greater than, at least 150% greater than, or at least 200% greater than the first indentation load deflection.

In some aspects, at least a portion of the first back facing side 36 of the first portion 30 fits within the central void space 50 defined by the second portion 40 so that at least 25% by volume of the first portion 30 is received within the central void space of the second portion. In further aspects, the first back facing surface 38 can be positioned alongside the second back facing surface 48 so that the first back facing surface 38 and the second back facing surface 48 cooperate to define a surface 29 (FIG. 1) of the second side 24 of the compressible pad 20.

In some aspects, the second side 24 of the compressible pad 20 can be planar or generally planar. In other aspects, the second side 24 of the compressible pad 20 can be concave. In other aspects, the second side 24 of the compressible pad 20 can be convex. In still other aspects, the second side 24 of the compressible pad 20 can be any other shape (e.g., wavy or otherwise uneven).

In some optional aspects, the compressible pad 20, in cross sections in planes parallel to the surface of the second side 24 of the compressible pad, can have a square, rectangular, or generally square or generally rectangular outer profile. In other aspects, the compressible pad 20, in cross sections in planes parallel to the surface of the second side 24 of the compressible pad, can have a circular, oval, or rounded profile. In still other aspects, the compressible pad 20, in cross sections in planes parallel to the surface of the second side of the compressible pad, can have any suitable profile. For example, optionally, the profile can match that of the shape of the electrode array 100.

In some optional aspects, all of the second portion 40 of the compressible pad 20 can be positioned peripherally around some or all of the first portion 30.

In some aspects, the compressible pad 20 can comprise foam. Optionally, in these aspects, the compressible pad 20 can comprise a first foam material 31 (FIG. 2) that defines the first portion 30 and a second foam material 41 (FIG. 3) that defines the second portion 40.

The first foam material 31 can have an outer peripheral surface 33. In some aspects, the second foam material 41 can be coupled to the outer peripheral surface 33 of the first foam material 31. For example, in some aspects, the first and second foam materials 31, 41 can be formed together via overmolding. In some aspects, the first and second foam materials 31, 41 can be adhered together (e.g., via adhesive or a fastener, such as hook and loop fastener). In other aspects, the first and second foam materials 31, 41 need not be coupled together. For example, in some aspects, the first foam material 31 can be removably received within the second foam material.

Referring to FIGS. 2-3, in some aspects, the first portion 30 of the compressible pad 20 can be removably coupled to the second portion 40. For example, in some aspects, the first portion can be coupled to the second portion via hook and loop fastener. For example, the first portion 30 and the second portion 40 of the compressible pad 20 can be coupled together using one or more patches or strips of hook and loop material 64 on each of the first portion and the second portion. Optionally, in these aspects, one of a hook fastener or a loop fastener can be positioned on the second front facing side 42 of the second portion 40 of the pad 20, and the other of the hook fastener or the loop fastener can be positioned on the first back facing side 36 of the first portion 30 of the pad 20. In other aspects, any suitable fastening means, such as, for example, adhesive, can be used to couple the first portion 30 of the compressible pad 20 to the second portion 40.

In some optional aspects, the first front facing surface 34 of the first front facing side 32 of the first portion 30 of the compressible pad 20 can have a convex surface in a direction away from the first back facing side 36. In some aspects, the first front facing surface 34 of the first front facing side 32 of the first portion 30 of the compressible pad 20 can have a surface shape comprising a partial spherical, ellipsoidal, paraboloidal or hyperboloidal shape. In other aspects, and as illustrated in FIG. 4, the first front facing surface 34 of the first front facing side 32 of the first portion 30 of the compressible pad 20 can comprise a plurality of planar or generally planar surfaces that meet at the apex 28.

In some aspects, the electrode array 100 can be coupled to, or otherwise held to, the apparatus 10 until the electrode array 100 is adhered to the skin of the user. For example, in some aspects, the apparatus 10 can comprise a hook and/or loop material 60 coupled on the first side 22 of the compressible pad 20. The hook and/or loop material 60 can be configured to releasably adhere to an electrode array 100. For example, in some aspects, the electrode array 100 can comprise an outer layer (e.g., cloth or nonwoven material) that releasably adheres to hook material coupled to the first side 22 of the compressible pad 20. In other aspects, the apparatus 10 can comprise an adhesive 62 coupled on the first side 22 of the compressible pad 20. The adhesive 62 can be configured to permit selective attachment and removal of an electrode array.

In some optional aspects, the compressible pad 20 can have a variable thickness. For example, the first side 22 of the compressible pad 20 can be spaced from the second side 24 along, or parallel to, the first axis 12 to define a thickness of the compressible pad, and the variable thickness can correspond to a distance between the first side and the second side along, or parallel to, the first axis 12. Optionally, in these aspects, the apex 28 can be positioned at the location of the greatest thickness of the compressible pad 20. Further, the thickness of the compressible pad can vary across the pad in dimensions perpendicular to the first axis 12.

Referring to FIG. 1, in some aspects, the apparatus can be coupled to a wall 110, or other surface (e.g., a chair). This can be advantageous for a user applying the electrode array to his/her/their back or other difficult to reach area. In some optional aspects, an adhesive 70 can be disposed on the second side 24 of the compressible pad 22. The adhesive 70 can couple the apparatus 10 to a wall 110 or other surface for application of the electrode array. In other aspects, the apparatus 10 can be coupled to the wall or other surface via one or more fasteners (e.g., screws or hook and loop material) or any other suitable fastening means.

Figure 5:
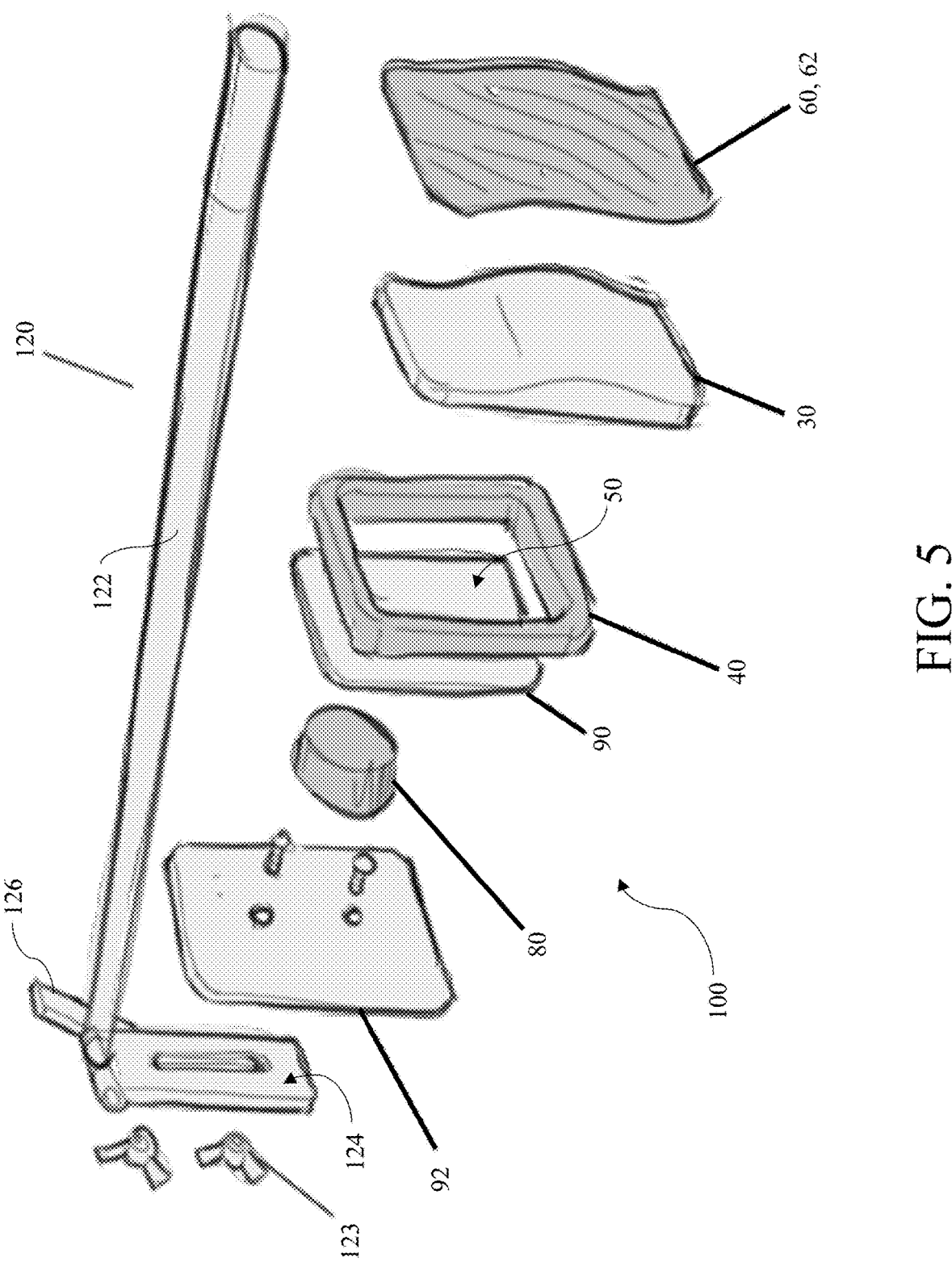
FIG. 5 is an exploded view of an assembly comprising an apparatus for applying an electrode array to skin of a user, as disclosed herein.

In some aspects, and with reference to FIG. 5, the apparatus 10 can be coupled to a handle 120. The user can use the handle to move the apparatus 10, with the electrode array coupled thereto, toward the user. In some aspects, the apparatus 10 can be coupled to a handle 120 via one or more fasteners 123. In some aspects, the handle 120 can comprise an arm 122 and a surface 124 to which the apparatus 10 is coupled. In some optional aspects, an angle between the arm 122 and the surface 124 can be adjustable (e.g., via a locking lever 126).

In some aspects, the apex 28 can be defined by a point. In some aspects, the apex 28 can be defined by an elongate ridge. In some aspects, the apex 28 can be defined by an area.

A second axis 14 can be perpendicular to the first axis 12, and a third axis 16 can be perpendicular to the first and second axes 12, 14 (FIG. 4). In some aspects, the apex 28 can be centered on the first front facing surface 34 of the first front facing side 32 of the first portion 30 of the compressible pad 20 along the second axis 14. In some aspects, the apex 28 can be centered on the first front facing surface 34 of the first front facing side 32 of the first portion 30 of the compressible pad 20 along the third axis 16. In other aspects, the apex can be spaced from the center of the first front facing surface 34 of the first front facing side 32 of the first portion 30 of the compressible pad 20 along the second axis 14 and/or along the third axis. That is, the apex 28 may or may not be centered on the first front facing surface 34.

Referring to FIG. 5, in some optional aspects, the apparatus 10 can comprise a support plate 90. The support plate 90 can be used for coupling the apparatus to a surface (e.g., a handle 120 or a wall 110 or chair). The support plate 90 can provide rigidity to the apparatus 10.

In some optional aspects, a spacer 80 can be received within the central void space 50. The spacer 80 can bias against the first portion 30 to inhibit the first portion from collapsing into the void space 50.

In some optional aspects, a mounting plate 92 can couple to the support plate 90. The mounting plate 92 can secure the apparatus to a desired surface, such as, for example, the surface 124.

System Comprising Apparatus for Applying Electrode Array

Referring to FIGS. 1-3, a system 200 can comprise an apparatus 10 as disclosed herein and an electrode array 100 coupled to the apparatus.

The electrode array 100 can have an outer surface 108. In some optional aspects, an entirety of the outer surface 108 of the electrode array can overlie the first (front-facing) side 22 of the compressible pad 20. Accordingly, an entirety of the peripheral edge 106 of the electrode array 100 can overlie the first (front-facing) side 22 of the compressible pad 20. In some aspects, the entirety of the peripheral edge 106 of the electrode array 100 can overlie the second front facing surface 44 of the second portion 40 compressible pad 20 (e.g., the electrode array covers the entire top face of FIG. 4, and the peripheral edge of the electrode array extends out, or near, to the outer edge of the top face).

In some aspects, an entirety of the outer surface 108 of the electrode array 100 can overlie at least a part of the first front facing surface 34 of the first portion 30 of the compressible pad 20. For example, when using the embodiment shown in FIG. 2, the outer surface 108 of the electrode array 100 can overlie at least a part of the first front facing surface 34 of the first portion 30 of the compressible pad 20. In other aspects, the entirety of the outer surface 108 of the electrode array 100 can overlie an area defined by a combination of at least a part of the first front facing surface 34 of the first portion 30 of the compressible pad 20 and at least part of the second front facing surface 44 of the second portion 40 of the compressible pad 20. For example, when using the embodiment shown in FIG. 4, outer portions of the outer surface 108 of the electrode array 100 can extend beyond the first front facing surface 34 of the first portion 30 of the compressible pad 20 and overlie portions of the second front facing surface 44 of the second portion 40 of the compressible pad 20.

In some aspects, the electrode array 100 can be coupled to the apparatus 10 by a hook and/or loop material 60 that is configured to releasably adhere the electrode array to the apparatus or an adhesive 62 that is configured to permit selective attachment and removal of the electrode array to and from the apparatus.

In some aspects, and as illustrated in FIGS. 2-3, a strap, belt, and/or tape 92 can circumferentially surround the compressible pad 20. For example, in some aspects, the strap, belt, and/or tape 92 can circumferentially surround the second portion 40 of the compressible pad 20.

Kit Comprising Apparatus for Applying Electrode Array

A kit can comprise an apparatus 10 as disclosed herein and at least one electrode array 100. In some aspects, the kit can comprise a plurality of electrode arrays 100.

Method of Using Apparatus for Applying Electrode Array

Disclosed herein is a method of using the apparatus 10 to apply an electrode array to a user, the electrode array comprising a skin-facing adhesive layer 102 and an outer surface 108 opposite the skin-facing adhesive layer, the skin-facing adhesive layer being configured for contacting skin of the user and having a peripheral edge 106. The method can comprise coupling the outer surface 108 of the electrode array 100 to the first side 22 of the apparatus 10. For example, the outer surface 108 can be coupled to the apparatus using hook and/or loop material 60 or adhesive 62.

The user can move toward the apparatus 10 to initiate contact of the apparatus with skin of the user. The skin of the user can initially contact an area of the skin-facing adhesive layer 102 within, and spaced from, the peripheral edge 106 of the skin-facing adhesive layer. This can be done by moving the apparatus and/or by moving the user. For example, the user can move toward the apparatus 10 with the apparatus being held stationary (e.g., on a wall). In another example, the apparatus 10 can be moved toward the user (e.g., via the handle 120). The user can continue to move toward the apparatus until the peripheral edge of the skin-facing adhesive layer is in contact with the skin of the user.

In some aspects, the electrode array 100 can comprise a release layer coupled to the skin-facing adhesive layer 102. In these aspects, the method can further comprise removing the release layer prior to moving the user toward the apparatus to initiate contact of the apparatus with skin of the user.

In some aspects, the skin of the user can be on the back of the user.

In some aspects, the apparatus 10 can be coupled to a wall 110 or a chair. Optionally, the method can further comprise coupling the apparatus 10 to the wall or the chair.

In some aspects, the apparatus can be coupled to a handle 120. Optionally, the method can further comprise coupling the apparatus 110 to the handle 120.

EXEMPLARY ASPECTS

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An apparatus for applying an electrode array to a body of a user, the apparatus comprising:

a compressible pad having a first side that is configured to face toward the user, and a second side that is configured to face away from the user, wherein the compressible pad comprises:

a first portion; and a second portion, wherein the first portion has a first front facing side having a first front facing surface and a first back facing side having a first back facing surface, wherein the first front facing side is spaced from the first back facing side in a front facing direction, wherein the second portion has a second front facing side having a second front facing surface and a second back facing side having a second back facing surface, and wherein the first front facing side is configured to face toward the user, wherein the second portion defines a central void space extending from the second front facing surface toward the second back facing surface, wherein the first front facing side extends outwardly in the front facing direction to form an apex.

Aspect 1A: The apparatus of aspect 1, wherein at least a portion of the first back facing side of the first portion is received within the central void space of the second portion.

Aspect 1B: The apparatus of aspect 1, wherein the first back facing surface of the first portion abuts the second front facing surface of the second portion Aspect 2: The apparatus of aspect 1, aspect 1A, or aspect 1B, wherein the first portion has a first indentation load deflection, and wherein the second portion has a second indentation load deflection that is greater than the first indentation load deflection of the first portion.

Aspect 3: The apparatus of aspect 1, aspect 1A, or aspect 1B, wherein at least a portion of the first back facing side of the first portion is received within the central void space of the second portion so that at least 25% by volume of the first portion is received within the central void space of the second portion, and wherein the first back facing surface is positioned alongside the second back facing surface such that the first back facing surface and the second back facing surface cooperate to define a surface of the second side of the compressible pad.

Aspect 4: The apparatus of any one of the preceding aspects, wherein the second side of the compressible pad is planar or generally planar.

Aspect 5: The apparatus of aspect 3 or aspect 4, wherein the compressible pad, in cross sections in planes parallel to the surface of the second side of the compressible pad, has a square, rectangular or generally square or generally rectangular outer profile.

Aspect 6: The apparatus of any of aspects 1-5, wherein all of the second portion is positioned peripherally around some or all of the first portion.

Aspect 7: The apparatus of any of aspects 1-6, wherein the compressible pad comprises a first foam material that defines the first portion and a second foam material that defines the second portion.

Aspect 8: The apparatus of aspect 7, wherein the first foam material has an outer peripheral surface, and wherein the second foam material is coupled to the outer peripheral surface of the first foam material.

Aspect 9: The apparatus of any one of the preceding aspects, wherein the first front facing surface of the first front facing side has a convex surface in a direction away from the first back facing side.

Aspect 10: The apparatus of any one of the preceding aspects, wherein the first front facing surface of the first front facing side has a surface shape comprising a partial spherical, ellipsoidal, paraboloidal or hyperboloidal shape.

Aspect 11: The apparatus of any one of the preceding aspects, further comprising a hook and/or loop material coupled on the first side of the compressible pad, wherein the hook and/or loop material is configured to releasably adhere to an electrode array.

Aspect 12: The apparatus of any one of the preceding aspects, further comprising an adhesive coupled on the first side of the compressible pad, wherein the adhesive is configured to permit selective attachment and removal of an electrode array.

Aspect 13: The apparatus of any one of the preceding aspects, further comprising an adhesive on the second side of the compressible pad.

Aspect 14: The apparatus of any one of the preceding aspects, wherein the first side of the compressible pad has an outer perimeter, and wherein the apex is spaced from the outer perimeter of the first side.

Aspect 15: The apparatus of any one of the preceding aspects, wherein the compressible pad comprises foam.

Aspect 16: The apparatus of any one of the preceding aspects, wherein the first surface is spaced from the second surface along a first axis to define a thickness of the compressible pad, wherein the thickness of the compressible pad varies across the pad when measured along, or parallel to, the first axis.

Aspect 17: The apparatus of aspect 1, wherein the first portion and the second portion are coupled together using one or more patches or strips of hook and loop material on each of the first portion and the second portion.

Aspect 18: An apparatus for applying an electrode array to a body of a user, the apparatus comprising:

a compressible pad having a first side that is configured to face toward the user, and a second side that is configured to face away from the user, wherein the first side extends outwardly in a front facing direction to form an apex.

Aspect 19: The apparatus of Aspect 18, wherein the compressible pad is formed from a single compressible material.

Aspect 20: A system comprising:

an apparatus as in any one of the preceding aspects; and an electrode array coupled to the apparatus.

Aspect 21: The system of aspect 20, wherein the electrode array has an outer surface, wherein an entirety of the outer surface of the electrode array overlies the compressible pad.

Aspect 22: The system of aspect 20, wherein the electrode array is coupled to the apparatus by a hook and/or loop material that is configured to releasably adhere the electrode array to the apparatus or an adhesive that is configured to permit selective attachment and removal of the electrode array to and from the apparatus.

Aspect 23: The system of any one of aspects 20-22, wherein the compressible pad comprises:

a first portion; and a second portion that at least partly peripherally surrounds the first portion, wherein the first portion has a first indentation load deflection, wherein the second portion has a second indentation load deflection that is greater than the first indentation load deflection of the first portion, wherein the first back facing surface of the first portion and the second back facing surface of the second portion cooperate to define a surface of the second side of the compressible pad, and wherein the electrode array has an outer perimeter, wherein an entirety of the outer perimeter of the electrode array overlies the compressible pad.

Aspect 24: The system of any one of aspects 20-22, wherein the compressible pad comprises:

a first portion; and a second portion;

wherein the first back facing surface of the first portion abuts the second front facing surface of the second portion;

wherein the first portion has a first indentation load deflection, wherein the second portion has a second indentation load deflection that is greater than the first indentation load deflection of the first portion; and wherein the electrode array has an outer perimeter, wherein an entirety of the outer perimeter of the electrode array overlies the compressible pad.

Aspect 25: A kit comprising:

an apparatus as in any one of the preceding aspects 1-19;

at least one electrode array.

Aspect 26: The kit of aspect 25, wherein the at least one electrode array comprises a plurality of electrode arrays.

Aspect 27: A method of using the apparatus as in any one of aspects 1-19 to apply an electrode array to a user, the electrode array comprising a skin-facing adhesive layer and an outer surface opposite the skin-facing adhesive layer, the skin-facing adhesive layer being configured for contacting skin of the user and having a peripheral edge, the method comprising:

coupling the outer surface of the electrode array to the first side of the apparatus;

moving the user toward the apparatus to initiate contact of the apparatus with skin of the user, wherein the skin of the user initially contacts an area of the skin-facing adhesive layer within, and spaced from, the peripheral edge of the skin-facing adhesive layer; and continuing to move the user toward the apparatus until the peripheral edge of the skin-facing adhesive layer is in contact with the skin of the user.

Aspect 28: The method of aspect 27, wherein the electrode array comprises a release layer coupled to the skin-facing adhesive layer, the method further comprising removing the release layer.

Aspect 29: The method of aspect 27 or aspect 28, wherein the skin of the user is on the back of the user.

Aspect 30: The method of any one of aspects 27-29, wherein the apparatus is coupled to a wall or a chair.

Aspect 31: The method of aspect 30, further comprising coupling the apparatus to the wall or the chair.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for applying an electrode array to a body of a user, the apparatus comprising:

a compressible pad having a first side that is configured to face toward the user, and a second side that is configured to face away from the user, wherein the compressible pad comprises:

a first portion; and a second portion, wherein the first portion has a first front facing side having a first front facing surface and a first back facing side having a first back facing surface, wherein the first front facing side is spaced from the first back facing side in a front facing direction, wherein the second portion has a second front facing side having a second front facing surface and a second back facing side having a second back facing surface, and wherein the first front facing side is configured to face toward the user, wherein the second portion defines a central void space extending from the second front facing surface toward the second back facing surface, wherein the first front facing side extends outwardly in the front facing direction to form an apex, and wherein either:

the first back facing surface of the first portion abuts the second front facing surface of the second portion, or at least a portion of the first back facing side of the first portion is received within the central void space of the second portion.

2. The apparatus of claim 1, wherein the first portion has a first indentation load deflection, and wherein the second portion has a second indentation load deflection that is greater than the first indentation load deflection of the first portion.

3. The apparatus of claim 1, wherein at least a portion of the first back facing side of the first portion is received within the central void space of the second portion so that at least 25% by volume of the first portion is received within the central void space of the second portion, and wherein the first back facing surface is positioned alongside the second back facing surface such that the first back facing surface and the second back facing surface cooperate to define a surface of the second side of the compressible pad.

4. The apparatus of claim 3, wherein the compressible pad, in cross sections in planes parallel to the surface of the second side of the compressible pad, has a square, rectangular, or generally square, or generally rectangular outer profile.

5. The apparatus of claim 1, wherein the second side of the compressible pad is planar or generally planar.

6. The apparatus of claim 1, wherein all of the second portion is positioned peripherally around some or all of the first portion.

7. The apparatus of claim 1, wherein the compressible pad comprises a first foam material that defines the first portion and a second foam material that defines the second portion.

8. The apparatus of claim 7, wherein the first foam material has an outer peripheral surface, and wherein the second foam material is coupled to the outer peripheral surface of the first foam material.

9. The apparatus of claim 1, wherein the first front facing surface of the first front facing side has a convex surface in a direction away from the first back facing side.

10. The apparatus of claim 1, wherein the first front facing surface of the first front facing side has a surface shape comprising a partial spherical, ellipsoidal, paraboloidal or hyperboloidal shape.

11. The apparatus of claim 1, further comprising a hook and/or loop material coupled on the first side of the compressible pad, wherein the hook and/or loop material is configured to releasably adhere to an electrode array.

12. The apparatus of claim 1, further comprising an adhesive coupled on the first side of the compressible pad, wherein the adhesive is configured to permit selective attachment and removal of an electrode array.

13. The apparatus of claim 1, further comprising an adhesive on the second side of the compressible pad.

14. The apparatus of claim 1, wherein the first side of the compressible pad has an outer perimeter, and wherein the apex is spaced from the outer perimeter of the first side.

15. The apparatus of claim 1, wherein the compressible pad comprises foam.

16. The apparatus of claim 1, wherein the first surface is spaced from the second surface along a first axis to define a thickness of the compressible pad, wherein the thickness of the compressible pad varies across the pad when measured along, or parallel to, the first axis.

17. The apparatus of claim 1, wherein the first portion and the second portion are coupled together using one or more patches or strips of hook and loop material on each of the first portion and the second portion.

18. A kit comprising:
an apparatus comprising:
a compressible pad having a first side that is configured to face toward the user, and a second side that is configured to face away from the user, wherein the compressible pad comprises:
a first portion; and
a second portion,
wherein the first portion has a first front facing side having a first front facing surface and a first back facing side having a first back facing surface, wherein the first front facing side is spaced from the first back facing side in a front facing direction, wherein the second portion has a second front facing side having a second front facing surface and a second back facing side having a second back facing surface, and wherein the first front facing side is configured to face toward the user,
wherein the second portion defines a central void space extending from the second front facing surface toward the second back facing surface,
wherein the first front facing side extends outwardly in the front facing direction to form an apex, and wherein either:
the first back facing surface of the first portion abuts the second front facing surface of the second portion, or
at least a portion of the first back facing side of the first portion is received within the central void space of the second portion; and
at least one electrode array.

19. A method of applying an electrode array to a user, the electrode array comprising a skin-facing adhesive layer and an outer surface opposite the skin-facing adhesive layer, the skin-facing adhesive layer being configured for contacting skin of the user and having a peripheral edge, the method comprising:
coupling the electrode array to an apparatus, the apparatus comprising:
a compressible pad having a first side that is configured to face toward the user, and a second side that is configured to face away from the user, wherein the compressible pad comprises:
a first portion; and
a second portion,
wherein the first portion has a first front facing side having a first front facing surface and a first back facing side having a first back facing surface, wherein the first front facing side is spaced from the first back facing side in a front facing direction, wherein the second portion has a second front facing side having a second front facing surface and a second back facing side having a second back facing surface, and
wherein the first front facing side is configured to face toward the user,
wherein the second portion defines a central void space extending from the second front facing surface toward the second back facing surface,
wherein the first front facing side extends outwardly in the front facing direction to form an apex, and wherein either:
the first back facing surface of the first portion abuts the second front facing surface of the second portion, or
at least a portion of the first back facing side of the first portion is received within the central void space of the second portion,
wherein coupling the electrode array to the apparatus comprises coupling the outer surface of the array to the first side of the compressible pad of the apparatus;
moving the user toward the apparatus to initiate contact of the apparatus with skin of the user, wherein the skin of the user initially contacts an area of the skin-facing adhesive layer within, and spaced from, the peripheral edge of the skin-facing adhesive layer; and
continuing to move the user toward the apparatus until the peripheral edge of the skin-facing adhesive layer is in contact with the skin of the user.

20. The method of claim 19, wherein the apparatus is coupled to a wall or a chair.

\* \* \* \* \*